United States Patent
Chen et al.

(10) Patent No.: US 9,757,355 B2
(45) Date of Patent: Sep. 12, 2017

(54) ORAL DOSAGE FORMS OF CYCLOPROPANECARBOXYLIC ACID {2-[(1S)-1-(3-ETHOXY-4-METHOXY-PHENYL)-2-METHANESULFONYL-ETHYL]-3-OXO-2,3-DIHYDRO-1H-ISOINDOL-4-YL}-AMIDE

(75) Inventors: Ming J. Chen, West Windsor, NJ (US);
Ho-Wah Hui, Basking Ridge, NJ (US);
Thomas Lee, Bedminster, NJ (US);
Paul Kurtulik, Branchburg, NJ (US);
Sekhar Surapaneni, Warren, NJ (US)

(73) Assignee: Celgene Corporation, Summit, NJ (US)

( * ) Notice: Subject to any disclaimer, the term of this patent is extended or adjusted under 35 U.S.C. 154(b) by 926 days.

(21) Appl. No.: 13/978,869

(22) PCT Filed: Jan. 9, 2012

(86) PCT No.: PCT/US2012/020579
§ 371 (c)(1),
(2), (4) Date: Dec. 19, 2013

(87) PCT Pub. No.: WO2012/096859
PCT Pub. Date: Jul. 19, 2012

(65) Prior Publication Data
US 2014/0093561 A1    Apr. 3, 2014

Related U.S. Application Data

(60) Provisional application No. 61/431,355, filed on Jan. 10, 2011.

(51) Int. Cl.
*A61K 31/4035* (2006.01)
*A61K 9/16* (2006.01)
*A61K 9/48* (2006.01)

(52) U.S. Cl.
CPC ........ *A61K 31/4035* (2013.01); *A61K 9/1617* (2013.01); *A61K 9/1635* (2013.01); *A61K 9/1652* (2013.01); *A61K 9/4825* (2013.01); *A61K 9/4833* (2013.01); *A61K 9/4858* (2013.01); *A61K 9/4866* (2013.01)

(58) Field of Classification Search
None
See application file for complete search history.

(56) References Cited

U.S. PATENT DOCUMENTS

| | | |
|---|---|---|
| 3,536,809 A | 10/1970 | Applezweig |
| 3,598,123 A | 8/1971 | Zaffaroni |
| 3,845,770 A | 11/1974 | Theeuwes et al. |
| 3,916,899 A | 11/1975 | Theeuwes et al. |
| 4,008,719 A | 2/1977 | Theeuwes et al. |
| 5,059,595 A | 10/1991 | Le Grazie |
| 5,073,543 A | 12/1991 | Marshall et al. |
| 5,120,548 A | 6/1992 | McClelland et al. |
| 5,354,556 A | 10/1994 | Sparks et al. |
| 5,591,767 A | 1/1997 | Mohr et al. |
| 5,639,476 A | 6/1997 | Oshlack et al. |
| 5,674,533 A | 10/1997 | Santus et al. |
| 5,733,566 A | 3/1998 | Lewis |
| 6,667,316 B1 | 12/2003 | Muller et al. |
| 6,962,940 B2 | 11/2005 | Muller et al. |
| 2004/0022861 A1 | 2/2004 | Williams et al. |
| 2007/0104780 A1 | 5/2007 | Lipari et al. |

FOREIGN PATENT DOCUMENTS

| | | | |
|---|---|---|---|
| WO | 99/45918 | 9/1999 | |
| WO | WO 99/45918 A1 | 9/1999 | |
| WO | WO 01/34606 A1 | 5/2001 | |
| WO | 03/086373 | 10/2003 | |
| WO | WO 03/086373 A1 | 10/2003 | |
| WO | 2004/043378 | 5/2004 | |
| WO | WO 2004/043378 A2 | 5/2004 | |
| WO | WO 2006/050057 A2 | 5/2006 | |
| WO | WO 2007/079182 A1 | 7/2007 | |
| WO | WO 2009/050289 A2 | 4/2009 | |
| WO | WO 2009087410 | * 7/2009 | ............... A61K 9/14 |
| WO | WO 2009/120296 A1 | 10/2009 | |
| WO | 2011/059931 | 5/2011 | |
| WO | WO 2011/059931 A2 | 5/2011 | |

OTHER PUBLICATIONS

Chokshi. IJPR 2004, 3: 3-16.*
The United States Pharmacopeia, 23rd Edition, United States Pharmacopeial Convention, Inc., Rockville, MD, pp. 1843-1844 (1995).
*Cancer: Principles & Practice of Oncology*, Third Edition, J. B. Lippincott Co., Philadelphia, PA, pp. 1843-1847 (1989).
Carstensen, Drug Stability: Principles & Practices, Second Edition, Marcel Dekker, New York, NY, pp. 379-380 (1995).
Muller et al., "Thalidomide analogs and PDE4 inhibition," Bioorg. & Med. Chem. Lett., 8:2669-2674 (1998).
Wolff ed., Burger's Medicinal Chemistry and Drug Discovery, 5th Edition, John Wiley & Sons, Inc., pp. 172-178, 949-982 (1995).

* cited by examiner

*Primary Examiner* — David J Blanchard
*Assistant Examiner* — Daniel F Coughlin
(74) *Attorney, Agent, or Firm* — Jones Day

(57) ABSTRACT

Provided herein are controlled release oral dosage forms of poorly soluble drugs, methods of making the dosage forms, and methods of their use for the treatment of various diseases and/or disorders.

5 Claims, 10 Drawing Sheets

ORAL DOSAGE FORMS OF CYCLOPROPANECARBOXYLIC ACID {2-[(1S)-1-(3-ETHOXY-4-METHOXY-PHENYL)-2-METHANESULFONYL-ETHYL]-3-OXO-2,3-DIHYDRO-1H-ISOINDOL-4-YL}-AMIDE

The present application is a 371 of International Application No. PCT/US2012/020579, filed Jan. 9, 2012, which claims priority to U.S. Provisional Patent Application No. 61/431,355, filed Jan. 10, 2011, the entirety of each of which is incorporated herein by reference.

1. FIELD OF INVENTION

Provided herein are oral dosage forms of cyclopropanecarboxylic acid {2-[(1S)-1-(3-ethoxy-4-methoxy-phenyl)-2-methanesulfonyl-ethyl]-3-oxo-2,3-dihydro-1H-isoindol-4-yl}-amide, methods of making the dosage forms, and methods of their use for the treatment of various diseases and/or disorders.

2. BACKGROUND OF THE INVENTION

One goal in developing a drug is to provide dosage forms which make it possible to maintain a certain amount or concentration of drug in a subject's body that will remain constant for several hours. Often this may not be achieved by traditional rapidly disintegrating tablets, as these tablets release the active ingredient contained therein all at once. For this reason, alternative dosage forms have been developed which are capable of improving the bioavailability of a drug upon oral administration. See, e.g., U.S. Patent Publication No. 2007/0104780.

Cyclopropanecarboxylic acid {2-[(1S)-1-(3-ethoxy-4-methoxy-phenyl)-2-methanesulfonyl-ethyl]-3-oxo-2,3-dihydro-1H-isoindol-4-yl}-amide (Compound A) has the following structure:

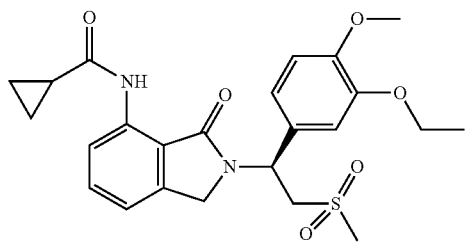 [SMILES: CCOc1cc([C@@H](CS(C)(=O)=O)N2Cc3cccc(NC(=O)C4CC4)c3C2=O)ccc1OC]

Compound A exhibits poor aqueous solubility (2 μg/mL), and is generally not suitable for oral administration by standard formulations. Thus, there exists a need for alternative formulations of Compound A in order to increase the bioavailability of the drug upon oral administration. Provided herein are oral dosage forms addressing this need.

3. SUMMARY OF THE INVENTION

Provided herein are oral dosage forms of cyclopropanecarboxylic acid {2-[(1S)-1-(3-ethoxy-4-methoxy-phenyl)-2-methanesulfonyl-ethyl]-3-oxo-2,3-dihydro-1H-isoindol-4-yl}-amide (Compound A), methods of making the dosage forms, and methods of their use for the treatment of various diseases and/or disorders.

The oral dosage forms provided herein comprise excipients which, when prepared according to the methods provided herein, increase the oral bioavailability of Compound A.

Without being bound to a particular theory, the oral dosage forms provided herein are believed to enhance the bioavailability of Compound A, a poorly soluble drug, by improving the solubility and dissolution rate of the drug in the gastrointestinal tract.

In one embodiment, provided herein is an oral dosage form comprising a compound of formula (I):

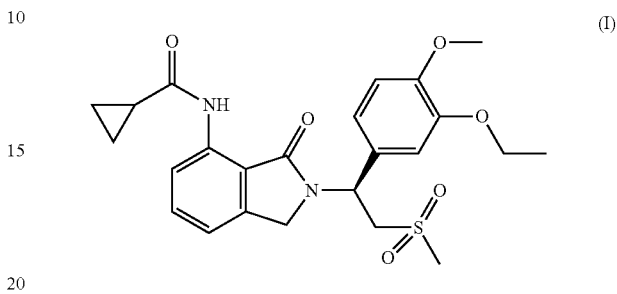

or a pharmaceutically acceptable salt thereof, wherein the oral dosage form further comprises mannitol, sodium croscarmellose, calcium stearate and one or more of the hydroxypropyl methylcellulose and polyvinylpyrrolidone-vinylacetate copolymer.

In another embodiment, provided herein is a method of preparing an oral dosage form comprising a compound of formula (I) by the following process:

(i) blend the compound of formula (I) with hydroxypropyl methylcellulose;

(ii) process the blended product of (i) by hot melt extrusion at 190° C.;

(iii) mill the extruded product of (ii) using 18 mesh screen;

(iv) blend the milled extrudate of (iii) with prescreened crosscarmellose sodium and mannitol;

(v) blend the product of (iv) with prescreened calcium stearate; and (vi) encapsulate the blended product of (v).

Also provided herein are methods of treating, preventing or managing disorders ameliorated by the reduction of levels of TNF-α in a patient which comprises administering to a patient in need of such treatment, prevention or management a therapeutically or prophylactically effective amount of Compound A, or a pharmaceutically acceptable prodrug, metabolite, polymorph, solvate, hydrate, or clathrate thereof, as formulated herein.

3.1. BRIEF DESCRIPTION OF THE FIGURES

3.2. DEFINITIONS

Figure 1:
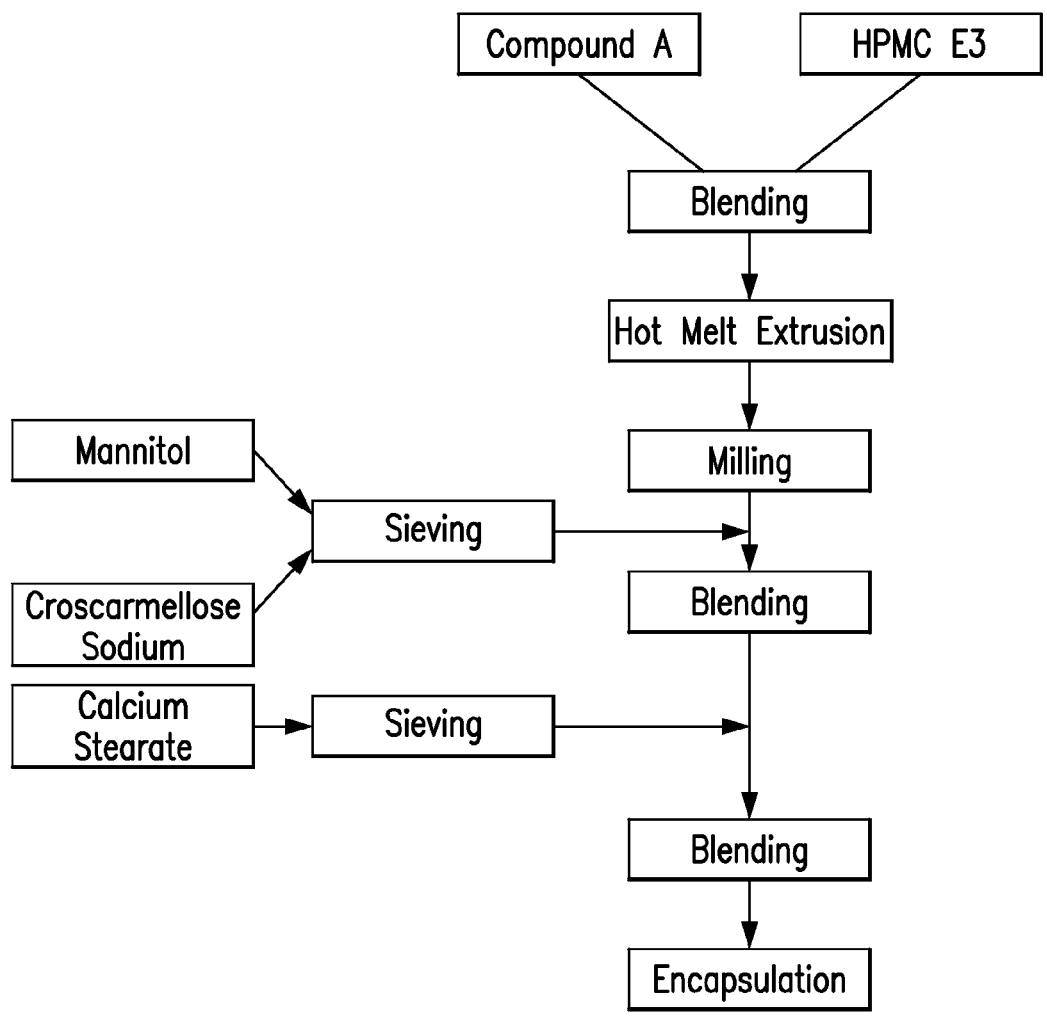
FIG. 1 shows a diagram for the preparation of hot melt extruded capsules of Compound A.

As used herein, the term "patient" refers to a mammal, particularly a human.

As used herein, the term "pharmaceutically acceptable salts" refer to salts prepared from pharmaceutically acceptable non-toxic acids or bases including inorganic acids and bases and organic acids and bases.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives and metabolites of a compound provided herein that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Prodrugs can typically be prepared using well-known methods, such as those described by 1 *Burger's Medicinal Chemistry and Drug Discovery,* 172-178, 949-982 (Manfred E. Wolff ed., 5th ed. 1995).

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "enantiomerically pure" means a stereomerically pure composition of a compound having one chiral center.

As used herein, term "adverse effects" includes, but is not limited to gastrointestinal, renal and hepatic toxicities, leukopenia, increases in bleeding times due to, e.g., thrombocytopenia, and prolongation of gestation, nausea, vomiting, somnolence, asthenia, dizziness, teratogenicity, extra-pyramidal symptoms, akathisia, cardiotoxicity including cardiovascular disturbances, inflammation, male sexual dysfunction, and elevated serum liver enzyme levels. The term "gastrointestinal toxicities" includes but is not limited to gastric and intestinal ulcerations and erosions. The term "renal toxicities" includes but is not limited to such conditions as papillary necrosis and chronic interstitial nephritis.

As used herein and unless otherwise indicated, the phrases "reduce or avoid adverse effects" and "reducing or avoiding adverse effects" mean the reduction of the severity of one or more adverse effects as defined herein.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

As used herein and unless otherwise specified, the term "crystalline" and related terms used herein, when used to describe a compound, substance, modification, material, component or product, unless otherwise specified, mean that the compound, substance, modification, material, component or product is substantially crystalline as determined by X-ray diffraction. See, e.g., *Remington: The Science and Practice of Pharmacy*, 21$^{st}$ edition, Lippincott, Williams and Wilkins, Baltimore, Md. (2005); *The United States Pharmacopeia*, 23$^{rd}$ ed., 1843-1844 (1995).

As used herein and unless otherwise specified, the term "crystal forms," "crystalline forms" and related terms herein refer to solid forms that are crystalline. Crystal forms include single-component crystal forms and multiple-component crystal forms, and include, but are not limited to, polymorphs, solvates, hydrates, and/or other molecular complexes. In certain embodiments, a crystal form of a substance may be substantially free of amorphous forms and/or other crystal forms. In certain embodiments, a crystal form of a substance may contain less than about 1%, 2%, 3%, 4%, 5%, 6%, 7%, 8%, 9%, 10%, 15%, 20%, 25%, 30%, 35%, 40%, 45% or 50% of one or more amorphous forms and/or other crystal forms on a weight basis. In certain embodiments, a crystal form of a substance may be physically and/or chemically pure. In certain embodiments, a crystal form of a substance may be about 99%, 98%, 97%, 96%, 95%, 94%, 93%, 92%, 91% or 90% physically and/or chemically pure.

As used herein and unless otherwise specified, the terms "solvate" and "solvated," refer to a crystal form of a substance which contains solvent. The terms "hydrate" and "hydrated" refer to a solvate wherein the solvent comprises water. "Polymorphs of solvates" refers to the existence of more than one crystal form for a particular solvate composition. Similarly, "polymorphs of hydrates" refers to the existence of more than one crystal form for a particular hydrate composition. The term "desolvated solvate," as used herein, refers to a crystal form of a substance which may be prepared by removing the solvent from a solvate.

As used herein and unless otherwise specified, the terms "about" and "approximately," when used in connection with a numeric value or a range of values which is provided to characterize a particular solid form, e.g., a specific temperature or temperature range, such as, e.g., that describing a DSC or TGA thermal event, including, e.g., melting, dehydration, desolvation or glass transition events; a mass change, such as, e.g., a mass change as a function of temperature or humidity; a solvent or water content, in terms of, e.g., mass or a percentage; or a peak position, such as, e.g., in analysis by IR or Raman spectroscopy or XRPD; indicate that the value or range of values may deviate to an extent deemed reasonable to one of ordinary skill in the art while still describing the particular solid form. For example, in particular embodiments, the terms "about" and "approximately," when used in this context and unless otherwise specified, indicate that the numeric value or range of values may vary within 25%, 20%, 15%, 10%, 9%, 8%, 7%, 6%, 5%, 4%, 3%, 2%, 1.5%, 1%, 0.5%, or 0.25% of the recited value or range of values.

As used herein and unless otherwise specified, a sample comprising a particular crystal form or amorphous form that is "substantially pure," e.g., substantially free of other solid forms and/or of other chemical compounds, contains, in particular embodiments, less than about 25%, 20%, 15%, 10%, 9%, 8%, 7%, 6%, 5%, 4%, 3%, 2%, 1%, 0.75%, 0.5%, 0.25% or 0.1% percent by weight of one or more other solid forms and/or of other chemical compounds.

As used herein and unless otherwise specified, a sample or composition that is "substantially free" of one or more other solid forms and/or other chemical compounds means that the composition contains, in particular embodiments, less than about 25%, 20%, 15%, 10%, 9%, 8%, 7%, 6%, 5%, 4%, 3%, 2%, 1%, 0.75%, 0.5%, 0.25% or 0.1% percent by weight of one or more other solid forms and/or other chemical compounds.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a patient with such a disease or disorder. In some embodiments, the terms refer to the administration of a compound provided herein, with or without other additional active agent, after the onset of symptoms of the particular disease.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of diseases or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. Often, the beneficial effects that a patient derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant that the diluent, excipient or carrier must be compatible with the other ingredients of the formulation and not deleterious to the recipient thereof.

4. DETAILED DESCRIPTION

Provided herein are oral dosage forms of cyclopropanecarboxylic acid {2-[(1S)-1-(3-ethoxy-4-methoxy-phenyl)-2-methanesulfonyl-ethyl]-3-oxo-2,3-dihydro-1H-isoindol-4-yl}-amide (Compound A), methods of making the dosage forms, and methods of their use for the treatment of various diseases and/or disorders.

The oral dosage forms provided herein comprise excipients which, when prepared according to the methods provided herein, increase the oral bioavailability of Compound A. Without being bound to a particular theory, the oral dosage forms provided herein are believed to enhance the bioavailability of Compound A, a poorly soluble drug, by improving the solubility and dissolution rate of the drug in the gastrointestinal tract.

The relative bioavailability of Compound A can be shown by a pharmacokinetic parameter, the area under the plasma concentration-time curve (AUC) of orally administered Compound A versus the AUC of a control ($AUC_{CONTROL}$). The relative bioavailability measures the bioavailability (estimated as the AUC) of a certain drug when compared with another formulation of the same drug. The $AUC_{CONTROL}$ is based on the human formulation in dry blend capsule as the control formulation, as stated in Example 5. In some embodiments, the oral dosage forms provided herein result in an increase in the bioavailability of Compound A by at least about 100%; 200% or 300%. In some embodiments, the improved bioavailability of Compound A results in an $AUC/AUC_{CONTROL}$ of at least about 3.0.

In some embodiments, the oral dosage forms provided herein are prepared by heat melt extrusion.

In some embodiments, the oral dosage forms provided herein are prepared by lipid-based emulsion techniques.

In some embodiments, the oral dosage forms provided herein are prepared by spray-dry and/or film formation techniques.

In other embodiments, the oral dosage forms provided herein are lipid formulations prepared by semi-solid microemulsion and/or self-(micro)-emulsified drug delivery techniques. In certain embodiments, the lipid formulations provided herein comprise one or more lipid-based excipient. Lipid based excipients are selected, for example, from Vitamin E, polyethoxylated castor oil (e.g., Cremophor RH 40, Cremophor EL or Cremophor ELP). In one embodiment, a combination of Vitamin E TPGS and Cremophor RH 40 is used.

In other embodiments, bioavailability of Compound A may be improved by particle size reduction, in addition to those methods described herein. In some embodiments, particle size reduction may be achieved by a nanoparticle micronization process. Such processes are appreciated by those of ordinary skill in the art. See, e.g., *Remington: The Science and Practice of Pharmacy*, 21st ed., Lippincott Williams & Wilkins, Philadelphia, Pa. (2005).

In certain embodiments, the oral dosage forms provided herein are in tablet or capsule form. In one embodiment, the oral dosage form is a tablet. In one embodiment, the oral dosage form is a capsule.

Provided herein are methods of treating, preventing or managing disorders ameliorated by the reduction of levels of TNF-α in a patient which comprises administering to a patient in need of such treatment, prevention or management a therapeutically or prophylactically effective amount of a compound provided herein, or a pharmaceutically acceptable prodrug, metabolite, polymorph, solvate, hydrate, or clathrate thereof.

In particular embodiments, diseases or disorders ameliorated by the inhibition of TNF-α production in mammals include, but are not limited to: HIV; hepatitis; adult respiratory distress syndrome; bone resorption diseases; chronic obstructive pulmonary diseases; chronic pulmonary inflammatory diseases; asthma; dermatitis; cystic fibrosis; septic shock; sepsis; endotoxic shock; hemodynamic shock; sepsis syndrome; post ischemic reperfusion injury; meningitis; psoriasis; fibrotic disease; cachexia; graft rejection; auto immune disease; rheumatoid spondylitis; arthritic conditions, such as psoriatic arthritis, rheumatoid arthritis and osteoarthritis; osteoporosis; Crohn's disease; ulcerative colitis; inflammatory bowel disease; multiple sclerosis; systemic lupus erythematosus; lupus nephritis; cutaneous lupus erythematosus; pulmonary sarcoidosis; erythema nodosum leprosum (ENL) in leprosy; radiation damage; asthma; and hyperoxic alveolar injury. Such disorders further include, but are not limited to, cancers, including, but not limited to cancer of the head, thyroid, neck, eye, skin, mouth, throat, esophagus, chest, bone, blood, bone marrow, lung, colon, sigmoid, rectum, stomach, prostate, breast, ovaries, kidney, liver, pancreas, brain, intestine, heart, adrenal, subcutaneous tissue, lymph nodes, heart, and combinations thereof. Specific cancers that can be treated by this method are multiple myeloma, malignant melanoma, malignant glioma, leukemia and solid tumors.

In some embodiments, provided herein are methods of treating or preventing cancer, including but not limited to, solid tumor and hematological cancers or hematological disorders and in particular, multiple myeloma, myelodysplastic syndrome, myeloprolifative disease, acute myeloid leukemia and chronic lymphocytic leukemiain a patient which comprises administering to a patient in need of such treatment or prevention a therapeutically effective amount of a compound provided herein, or a pharmaceutically acceptable prodrug, metabolite, polymorph, solvate, hydrate, or clathrate thereof; in particular wherein the patient is a mammal.

In another embodiment provided herein is a method of inhibiting PDE4 which comprises contacting PDE4 in a cell (e.g. a mammalian cell) with an effective amount of a compound provided herein, or a pharmaceutically acceptable prodrug, metabolite, polymorph, solvate, hydrate, or clathrate thereof (wherein particular embodiments encompass solid forms comprising Compound A as described herein).

In further embodiments, provided herein are methods of treating or preventing diseases or disorders ameliorated by the inhibition of PDE4 in a patient which comprises administering to a patient in need of such treatment or prevention a therapeutically or prophylactically effective amount of a compound provided herein, or a pharmaceutically acceptable prodrug, metabolite, polymorph, solvate, hydrate, or clathrate thereof. Disorders ameliorated by the inhibition of PDE4 include, but are not limited to, asthma, inflammation (e.g., inflammation due to reperfusion), chronic or acute obstructive pulmonary diseases, inflammatory pneumonitis, chronic or acute pulmonary inflammatory diseases, inflammatory bowel disease, Crohn's Disease, Behcet's Disease, cutaneous lupus erythematosus, or colitis.

In other embodiments, provided herein are methods of controlling cAMP levels in a cell which comprises contacting a cell with an effective amount of a compound provided herein, or a pharmaceutically acceptable prodrug, metabolite, polymorph, solvate, hydrate, or clathrate thereof. As used herein the term "controlling cAMP levels" includes preventing or reducing the rate of the breakdown of Adenosine 3',5'-cyclic monophosphate (cAMP) in a cell or increasing the amount of Adenosine 3',5'-cyclic monophosphate present in a cell, preferably a mammalian cell, more preferably a human cell. In a particular method, the rate of cAMP breakdown is reduced by about 10, 25, 50, 100, 200, or 500 percent as compared to the rate in comparable cells which have not been contacted with a compound of the invention.

In other embodiments, provided herein are methods of treating or preventing depression, asthma, inflammation, contact dermatitis, atopic dermatitis, psoriasis, psoriatic arthritis, rheumatoid arthritis, osteoarthritis, inflammatory skin disease, inflammation due to reperfusion, chronic or acute obstructive pulmonary diseases, chronic or pulmonary inflammatory diseases, inflammatory bowel disease, Crohn's Disease, Behcet's Disease or colitis in a patient which comprises administering to a patient in need of such treatment or prevention a therapeutically or prophylactically effective amount of a compound provided herein, or a pharmaceutically acceptable prodrug, metabolite, polymorph, solvate, hydrate, or clathrate thereof; in particular wherein the patient is a mammal.

In some methods herein, a compound provided herein, or a pharmaceutically acceptable polymorph, prodrug, solvate, hydrate, or clathrate thereof, is adjunctively administered with at least one additional therapeutic agent. Examples of additional therapeutic agents include, but are not limited to, anti-cancer drugs, anti-inflammatories, antihistamines and decongestants.

4.1. Methods of Manufacture

Formulations of Compound A may be prepared according to the following methods of manufacture.

Solid dispersions of Compound A may be prepared for use as described herein by (i) blending Compound A with hydroxypropyl methylcellulose (HPMC); (ii) processing the resulting blend by hot melt extrusion; (iii) milling the extruded product; (iv) blending the milled extrudate with prescreened crosscarmellose sodium and mannitol; (v) blending the product with prescreened calcium stearate; and (vi) encapsulating the blended product.

Lipid-based formulations of Compound A may be prepared for use as described herein by melting one or more lipid-based expicients, combining with Compound A, and filling the resulting product into gelatin capsules. In certain embodiments, the lipid based excipient(s) are selected from Vitamin E TPGS, and polyethoxylated castor oil (e.g., Cremophor RH 40, Cremophor EL or Cremophor ELP). In one embodiment, a combination of Vitamin E TPGS and Cremophor RH 40 is used.

Spray-dry formulations of Compound may be prepared for use as described herein by dissolving Compound A with one or more excipients in a solvent, and spray-drying the drug solution. In certain embodiments, the one or more excipients is selected from hydroxylpropyl methyl cellulose (e.g., HPMC E3, HPMC E5), poly(butyl methacrylate-co-2-dimethylaminoethyl methacrylate-co-methyl methacrylate) (1:2:1) (Eudragit® E PO), polyvinylpyrrolidone (e.g. PVP K12) and a polyvinylpyrrolidone-vinylacetate copolymer (e.g., PVP VA 64, Kollidon® VA64).

The Examples herein provide specific formulations prepared according to the methods above.

4.2. Pharmaceutical Compositions

Pharmaceutical compositions and dosage forms provided herein typically also comprise one or more pharmaceutically acceptable excipient, diluent or carrier.

In some embodiments, a pharmaceutical composition provided herein comprises one or more solid forms a compound provided herein and at least one additional therapeutic agent. Examples of additional therapeutic agents include, but are not limited to: anti-cancer drugs and anti-inflammation therapies including, but not limited to, those provided herein.

Examples of oral dosage forms include, but are not limited to: tablets; caplets; capsules, such as soft elastic gelatin capsules; cachets; troches; lozenges; dispersions; aerosols (e.g., inhalers); gels; liquid dosage forms suitable for oral administration to a patient, including suspensions (e.g., aqueous or non-aqueous liquid suspensions, oil-in-water emulsions, or a water-in-oil liquid emulsions), solutions, and elixirs.

The composition, shape, and type of dosage forms provided herein will typically vary depending on their use. These variations will be readily apparent to those skilled in the art. See, e.g., *Remington: The Science and Practice of Pharmacy*, 21st ed., Lippincott Williams & Wilkins, Philadelphia, Pa. (2005).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form.

Lactose-free compositions of the invention can comprise excipients that are well known in the art and are listed, for example, in the U.S. Pharmocopia (USP) SP (XXI)/NF (XVI). In general, lactose-free compositions comprise an active ingredient, a binder/filler, and a lubricant in pharmaceutically compatible and pharmaceutically acceptable amounts. Preferred lactose-free dosage forms comprise an active ingredient, microcrystalline cellulose, pre-gelatinized starch, and magnesium stearate.

This invention further encompasses anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the invention can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The dosage forms provided herein may further comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms provided herein lie within the range of from about 1 mg to about 1,000 mg per day, given as a single once-a-day dose in the morning but preferably as divided doses throughout the day. More specifically, the daily dose is administered twice daily in equally divided doses. Specifically, a daily dose range may be from about 5 mg to about 500 mg per day, more specifically, between about 10 mg and about 200 mg per day. In managing the patient, the therapy may be initiated at a lower dose, perhaps about 1 mg to about 25 mg, and increased if necessary up to about 200 mg to about 1,000 mg per day as either a single dose or divided doses, depending on the patient's global response.

The oral dosage forms provided herein may be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally *Remington's Pharmaceutical Sciences*, 18th ed., Mack Publishing, Easton Pa. (1990).

Typical oral dosage forms provided herein are prepared by combining the active ingredient(s) in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the invention is typically present in from about 50 to about 99 weight percent of the pharmaceutical composition or dosage form.

Suitable forms of microcrystalline cellulose include, but are not limited to, the materials sold as AVICEL-PH-101™, AVICEL-PH-103™, AVICEL RC-581™, AVICEL-PH-105™ (available from FMC Corporation, American Viscose Division, Avicel Sales, Marcus Hook, Pa.), and mixtures thereof. A specific binder is a mixture of microcrystalline cellulose and sodium carboxymethyl cellulose (sodium CMC) sold, for example, as AVICEL RC-581™. Suitable anhydrous or low moisture excipients or additives include AVICEL-PH-103™ and Starch 1500 LM™.

Disintegrants may be used in the compositions herein to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that may be used herein include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that may be used herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200™, manufactured by W.R. Grace Co. of Baltimore, Md.), a coagulated aerosol of synthetic silica (marketed by Degussa Co. of Plano, Tex.), CAB-O-SIL™ (a pyrogenic silicon dioxide product sold by Cabot Co. of Boston, Mass.), and mixtures thereof. If used at all, lubricants are typically used in an amount of less than about one weight percent of the pharmaceutical compositions or dosage forms into which they are incorporated.

Dosage forms comprising a compound may be administered by controlled release means or by delivery devices that are well known to those of ordinary skill in the art. Examples include, but are not limited to, those described in U.S. Pat. Nos. 3,536,809; 3,598,123; 3,845,770; 3,916,899; 4,008,719; 5,059,595; 5,073,543; 5,120,548; 5,354,556; 5,591,767; 5,639,476; 5,674,533 and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients of the invention. The invention thus encompasses single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

4.3. Methods of Treatment

The invention encompasses methods of treating, preventing and managing diseases or disorders ameliorated by the reduction of levels of TNF-α in a patient which comprise administering to a patient in need of such treatment, prevention or management a therapeutically or prophylactically effective amount of a controlled release oral dosage form provided herein.

Disorders ameliorated by the inhibition of TNF-α include, but are not limited to: heart disease, such as congestive heart failure, cardiomyopathy, pulmonary edema, endotoxin-mediated septic shock, acute viral myocarditis, cardiac allograft rejection, and myocardial infarction; solid tumors, including but not limited to, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, and retinoblastoma; and bloodborne tumors including but not limited to, acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", hairy cell leukemia, multiple myeloma and acute and chronic leukemias, for example, lymphoblastic, myelogenous, lymphocytic, and myelocytic leukemias.

Specific methods provided herein further comprise the administration of an additional therapeutic agent. Examples of additional therapeutic agents include, but are not limited to, anti-cancer drugs such as, but are not limited to: alkylating agents, nitrogen mustards, ethylenimines, methylmelamines, alkyl sulfonates, nitrosoureas, triazenes, folic acid analogs, pyrimidine analogs, purine analogs, vinca alkaloids, epipodophyllotoxins, antibiotics, topoisomerase inhibitors and anti-cancer vaccines.

Specific additional therapeutic agents include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2;

axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; episteride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

Embodiments herein further encompass a method of treating or preventing diseases or disorders ameliorated by the inhibition of PDE4 in a patient. Disorders ameliorated by the inhibition of PDE4 include, but are not limited to, asthma, inflammation, macular degeneration, chronic or acute obstructive pulmonary disease, chronic or acute pulmonary inflammatory disease, inflammatory bowel disease, Crohn's Disease, Behcet's Disease, cutaneous lupus erythematosus, colitis, ulcerative colitis and arthritis or inflammation due to reperfusion. In another embodiment, the diseases or disorders to be treated may be diseases of the lung, chronic obstructive pulmonary disease or inflammatory pneumonitis.

Specific methods provided herein may comprise the administration of an additional therapeutic agent such as, but not limited to, anti-inflammatory drugs, antihistamines and decongestants. Examples of such additional therapeutic agents include, but are not limited to: antihistamines including, but not limited to, ethanolamines, ethylenediamines, piperazines, and phenothiazines; antinflammatory drugs; NSAIDS, including, but not limited to, aspirin, salicylates, acetominophen, indomethacin, sulindac, etodolac, fenamates, tolmetin, ketorolac, diclofenac, ibuprofen, naproxen, fenoprofen, ketoprofen, flurbiprofen, oxaprozin, piroxicam, meloxicam, pyrazolon derivatives; and steriods including, but not limited to, cortical steroids and adrenocortical steroids.

As stated above, the dosage forms provided herein may be used in the treatment or prevention of a wide range of diseases and conditions. The magnitude of a prophylactic or therapeutic dose of a particular active ingredient of the invention in the acute or chronic management of a disease or condition may vary with the nature and severity of the disease or condition and the route by which the active ingredient is administered. The dose, and perhaps the dose frequency, will also vary according to the age, body weight, and response of the individual patient. Suitable dosing regimens can be readily selected by those skilled in the art with due consideration of such factors. In general, the recommended daily dose range for the conditions described herein lie within the range of from about 1 mg to about 1,000 mg per day, given as a single once-a-day dose preferably as divided doses throughout a day. More specifically, the daily dose is administered twice daily in equally divided doses. Specifically, a daily dose range may be from about 5 mg to about 500 mg per day, more specifically, between about 10 mg and about 200 mg per day. Specifically, the daily dose may be administered in 5 mg, 10 mg, 15 mg, 20 mg, 25 mg, 30 mg, 50 mg, or 100 mg dosage forms (Q.D. or B.I.D.). In managing the patient, the therapy should be initiated at a lower dose, perhaps about 1 mg to about 25 mg, and increased if necessary up to about 200 mg to about 1,000 mg per day as either a single dose or divided doses, depending on the patient's global response. Alternatively, the daily dose is from 0.01 mg/kg to 100 mg/kg.

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

4.3.1. Kits

This invention encompasses kits which, when used by the medical practitioner, can simplify the administration of appropriate amounts of active ingredients to a patient.

A typical kit of the invention comprises a unit dosage form of a compound provided herein, or a pharmaceutically acceptable solid form or prodrug thereof, and a unit dosage form of a second active ingredient. Examples of second active ingredients include, but are not limited to, those listed herein.

Kits of the invention can further comprise devices that are used to administer the active ingredient(s). Examples of such devices include, but are not limited to, syringes, drip bags, patches, and inhalers.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

5. EXAMPLES

Certain embodiments of the invention are illustrated by the following non-limiting examples. The present application incorporates by reference the entirety of U.S. Pat. No. 6,962,940, including the Examples provided therein.

5.1. Example 1: Synthesis of cyclopropanecarboxylic acid {2-[(1S)-1-(3-ethoxy-4-methoxy-phenyl)-2-methane-sulfonyl-ethyl]-3-oxo-2,3-dihydro-1H-isoindol-4-yl}-amide Preparation of methyl 2-methyl-6-nitrobenzoate A mixture of 2-methyl-6-nitrobenzoic acid (300.0 g, 1.66 moles, from Acros Organics, Morris Plains, N.J.) and trimethyl orthoacetate (298.3 g, 2.48 moles, from Aldrich Chemicals, Milwauke, Wis.) was charged into a 3-L 3-necked flask at about 20-25° C. under nitrogen. The reaction mixture was gradually heated and the low-boiling point components generated during the reaction were distilled off to an internal temperature of 95-100° C. After 2 hours, the reaction mixture was cooled to 20-25° C. over 1-2 hours. After heptane (1.50 L, from Aldrich Chemicals) was charged into the reaction mixture over 1.0-1.5 hours, the reaction mixture was seeded with methyl 2-methyl-6-nitrobenzoate (0.5 g) when it became turbid. The suspension was cooled to 0-5° C. over 0.5-1 hour and kept at 0-5° C. for another 1.5-2 hours. The solid was collected by filtration under vacuum, washed with heptane (3×300 mL), and dried to a constant weight in a tray at 30-35° C. under a vacuum at 100-120 torr. The yield of methyl 2-methyl-6-nitrobenzoate was 292.0 g (91%), based on 300.0 g of 2-methyl-6-nitrobenzoic acid. The product was found to have a purity of >99% measured by HPLC based on area percentage, and a water content of <0.1% measured by Karl Fisher titration.

Preparation of methyl 2-bromomethyl-6-nitrobenzoate

A mixture of methyl 2-methyl-6-nitrobenzoate (200.0 g, 1.02 moles, previously prepared), 1,3-dibromo-5,5-dimethylhydantoin (DBH, 162.0 g, 0.57 mole, from Aldrich Chemicals) and methyl acetate (1.20 L, from Aldrich Chemicals) was charged into a 3-L three-necked flask at about 20-25° C. under nitrogen. After the reaction mixture was refluxed for 0.5-1 hour, a solution of 2,2'-azobisisobutyronitrile (AIBN, 8.6 g, 52 mmol, from Aldrich Chemicals) in 100 mL of methyl acetate was charged over 15-30 minutes. The reaction mixture was refluxed for 6.5-8 hours until the amount of unreacted 2-methyl-6-nitrobenzoate was less than 5-10%. The reaction mixture was cooled to 15-18° C. and kept at 15-18° C. for 50-60 minutes. The solid was filtered, washed with cold (i.e., 5-10° C.) methyl acetate (2×100 mL) until there was less than 3% of methyl 2-bromomethyl-6-nitrobenzoate remained in the solid. Next, after heptane (1.00 L) was charged into the filtrate, the upper layer organic phase was washed with 2% of brine (2×500 mL) and deionized water (1-2×500 mL) until there was less than 0.5% (area percentage at 210 nm) of unreacted 5,5-dimethylhydantoin according to measurement by HPLC. After the solution was concentrated under a reduced pressure to remove about 1.80-1.90 L of methyl acetate, methyl tertbutyl ether (MTBE, 300 mL) was charged. After the reaction mixture was refluxed at 65-70° C. for 10-15 minutes, the solution was cooled to 50-55° C. over 0.5-1 hour and seeded with 500 mg of methyl 2-bromomethyl-6-nitrobenzoate at 45-50° C. The suspension was cooled to 20-25° C. and kept at 20-25° C. for 2-3 hours. The solids were collected by filtration, washed with 5-10° C. a cold mixture of heptane and MTBE in a volume ratio of 1:2 (2×100 mL), and dried to a constant weight at 20-25° C. under a vacuum at 100-120 torr. The yield of methyl 2-bromomethyl-6-nitrobenzoate was 185.2 g (66%), based on 200.0 g input of methyl 2-methyl-6-nitrobenzoate. The product was found to have a purity of >98% measured by HPLC based on area percentage, and a water content of <0.1% measured by Karl Fisher titration.

Preparation of (1S)-1-(3-ethoxy-4-methoxyphenyl)-2-methanesulfonyl-ethylamine

After a mixture of (1S)-1-(3-ethoxy-4-methoxyphenyl)-2-methanesulfonyl-ethylamine N-acetyl-L-Leucine salt (1.10 kg, 2.46 moles), deionized water (4.40 L), and dichloromethane (DCM, 5.50 L) was charged into a reaction vessel, a solution of sodium hydroxide (196.0 g, 4.90 moles) in 1.00 L of deionized water was charged into the reaction vessel over about 5 minutes at 15-25° C. The resulting mixture was stirred for at least 10 minutes at 15-25° C. and then the aqueous and organic phases were allowed to separate. The pH of the upper aqueous phase was maintained or adjusted at pH 13-14. The phases were separated and the upper aqueous phase was extracted with DCM (2×4.4 L). The pH of the aqueous phase was maintained at 13-14 throughout the extractions. The DCM extracts were combined and washed with deionized water (3.3 L) until the pH of the aqueous phase reached 11 or less. DCM was removed under vacuum below 35° C. The water content of the residual solid should be <0.1% w/w as measured by Karl Fisher titration. The residual solid was dried azeotropically with more DCM. The solid was dried to a constant weight in vacuo at 30-35° C. to give (1S)-1-(3-ethoxy-4-methoxyphenyl)-2-methanesulfonyl-ethylamine as a white powder (639.0-672.0 g, 95-100% yield).

Preparation of (1S)-7-nitro-2-[1-(3-ethoxy-4-methoxyphenyl)-2-(methylsulfonyl)ethyl]isoindolin-1-one (1S)-7-nitro-2-[1-(3-ethoxy-4-methoxyphenyl)-2-(methylsulfonyl)ethyl]isoindolin-1-one was prepared by the following procedure. A mixture of methyl 2-bromomethyl-6-nitrobenzoate (100.0 g, 365 mmol, prepared previously in Example 5.7.2), (1S)-1-(3-ethoxy-4-methoxyphenyl)-2-methanesulfonylethylamine (104.7 g, 383 mmol, prepared previously in Example 5.7.3), sodium hydrogen carbonate (67.5 g, 8.03 moles, from Aldrich Chemicals) and dimethyl formamide (500 mL) was charged into a 1-L 3-necked flask at room temperature under nitrogen. The reaction mixture was gradually heated to an internal temperature of 70-75° C. for two hours until there was less than <2% of unreacted methyl 2-bromomethyl-6-nitrobenzoate. The reaction mixture was gradually heated to an internal temperature of 95-100° C. for 18 hours. The reaction mixture was cooled to 20-25° C. and transferred to an 1-L addition funnel. After purified water (1500 mL) was charged into a 5-L 3-necked flask, the reaction mixture in the addition funnel was added into water in the 5-L 3-necked flask at room temperature over 1-2 hours maintaining an internal temperature below 30° C. The reaction mixture was stirred for 2 hours at room temperature. The solid was filtered out under vacuum, washed with water (3×300 mL) and methanol (2×400 mL), and then charged into a 2-L 3-necked flask followed by methanol (1000 mL). The mixture was refluxed for 1 hour. The mixture was cooled to room temperature. The solid was collected by filtration under vacuum, washed with 200 mL methanol (2 vol), and dried to a constant weight at 40-45° C. under a vacuum at 100-120 torr. The yield of (1S)-7-nitro-2-[1-(3-ethoxy-4-methoxyphenyl)-2-(methylsulfonyl)ethyl] isoindolin-1-one was 123.0 g (78%), based on 100.0 g input of methyl 2-bromomethyl-6-nitrobenzoate. The product was found to have a purity of >99% measured by HPLC based on area percentage, and a water content of <0.1% measured by Karl Fisher titration Alternative Preparation of (1S)-7-nitro-2-[1-(3-ethoxy-4-methoxyphenyl)-2-(methylsulfonyl)ethyl]isoindolin-1-one (1S)-7-nitro-2-[1-(3-ethoxy-4-methoxyphenyl)-2-(methylsulfonyl)ethyl]isoindolin-1-one was also prepared by the following procedure. A mixture of methyl 2-bromomethyl-6-nitrobenzoate (100.0 g, 365 mmol, prepared previously in Example 5.7.2), (1S)-1-(3-ethoxy-4-methoxyphenyl)-2-methanesulfonyl-ethylamine (104.7 g, 383 mmol, prepared previously in Example 5.7.3), and potassium carbonate powder (100.8 g, 730 mmol, from Aldrich Chemicals) was suspended in acetonitrile (500 mL) at room temperature. The reaction mixture was refluxed at 81-83° C. for about two hours until there was less than 2% of unreacted methyl 2-bromomethyl-6-nitrobenzoate. After the reaction mixture was cooled to 45-50° C., methanol (200 mL) was charged over 5-10 minutes. After the mixture was allowed to cool to 20-25° C. and stirred for 2 hours, deionized water (1.40 L) was charged over 0.5-1 hour and stirred at 20-25° C. for 30 minutes and at 0-5° C. for 1-2 hours. The solid was filtered, washed with deionized water (3×300 mL), and dried to <10% of water content as measured by Karl Fisher titration. The solid was suspended in methanol (750 mL) and refluxed for 1-1.5 hours. The suspension was cooled to 0-5° C. over 1.5-2 hours and kept at 0-5° C. for 1-1.5 hours. The solid was filtered, washed with 0-5° C. methanol (2×200 mL) and heptane (200 mL), and then dried at 40-45° C. under vacuum to a constant weight. The yield of (1S)-7-nitro-2-[1-(3-ethoxy-4-methoxyphenyl)-2-(methylsulfonyl)ethyl]isoindolin-1-one was 148.0 g (93%), based on 100.0 g input of methyl 2-bromomethyl-6-nitrobenzoate. The product was found to have a purity of >99% measured by HPLC based on area percentage, and a water content of <1.0% measured by Karl Fisher titration.

Preparation of Compound A

A mixture of (1S)-7-nitro-2-[1-(3-ethoxy-4-methoxyphenyl)-2-(methylsulfonyl)ethyl]isoindolin-1-one (60 g, 138 mmol, prepared previously in Example 5.7.5), 10% Pd/C (50% wet, 2.4 g, 4 wt %, from Johnson Matthey, London, UK), ethyl acetate (780 mL) was charged into a Parr-vessel at room temperature under nitrogen. After the mixture was purged with nitrogen three times and with hydrogen three times, the reaction mixture was heated to 40° C. and then the heat was removed. The reaction mixture was stirred with hydrogen at a pressure between 40-45 psi over 4-6 hours until there was <3% of the hydroxylamine intermediate. The reaction mixture was cooled to 20-25° C. The reaction mixture was filtered through a celite bed (1 inch thickness) and then bed-washed with ethyl acetate (120 mL). The filtrate was transferred to a 3-L 3-necked flask equipped with a 50-mL addition funnel. After N,N-diisopropylethylamine (29 mL, 165 mmol) was charged into the flask, the addition funnel was charged with cyclopropylcarbonyl chloride (13.0 mL, 145 mmol, from Aldrich Chemicals). The cyclopropylcarbonyl chloride was added at room temperature over 1-2 hours at an internal temperature below 30° C. The reaction mixture was stirred for 2-4 hours at room temperature. After heptane (300 mL) was added, the reaction mixture was stirred for 4-6 hours. The solid was collected by filtration under vacuum, washed with 2N HCl (2×300 mL), water (2×300 mL) and then heptane (2×300 mL). The crude product was dried at 40-45° C. under a vacuum at 100-120 torr to a constant weight. The yield of crude Compound (1) was 58 g (88%), based on 60.0 g input of (1S)-7-nitro-2-[1-(3-ethoxy-4-methoxyphenyl)-2-(methylsulfonyl)ethyl]-isoindolin-1-one.

Recrystallization of Compound A

A mixture of crude Compound (1) (95.2 g, prepared previously in Example 5.7.6) and tetrahydrofuran (THF, 1.43 L) was charged into a 3 L flask at 20-25° C. under nitrogen. The suspension was heated to 60-65° C. until dissolution was achieved. The suspension was filtered at 45-50° C. and the solid was rinsed with 95 mL of THF prewarmed at 45-55° C. After about 950-1150 mL of THF was distilled off at normal pressure over 30-60 minutes, absolute ethanol (950 mL) was charged at 55-60° C. over 5-10 minutes. About 350-400 mL of solvents was removed at normal pressure until the internal temperature rose to 72-74° C. The resulting suspension was refluxed at 72-75° C. for 30-60 minutes, cooled to 20-25° C. over 1-2 hours and kept at 20-25° C. for another 1-2 hours. The solid was collected by filtration under vacuum, washed with absolute ethanol (240-280 mL) and heptane (240-280 mL), and then dried in tray at 50-55° C. in a vacuum at 130-140 torr to a constant weight. The yield of the off-white crystalline product was (88.0-91.0 g, 92-96%).

5.2. Example 2: Heat Melt Extrusion Formulation 1

Formulation 1, a solid powder dispersion of Compound A, was prepared as follows:

1. Blend Compound A with HPMC for 460 rotations using a Turbula® mixer;
2. Process the blended Compound A by hot melt extrusion at 190° C.;
3. Mill the extruded product using 18 mesh screen;
4. Blend the milled extrudate with prescreened (35 mesh) crosscarmellose sodium and mannitol M200 for 460 rotations;
5. Blend the product with prescreened calcium stearate for 75 rotations; and
6. Encapsulate the blended product using a semi-automatic encapsulator.

The above method results in a physically stable solid dispersion of Compound A having an aqueous solubility of about 2 µg/mL.

| Formulation 1 | Amount (mg) | % |
|---|---|---|
| Compound A | 50.0 | 9.0 |
| HPMC E3 | 283.3 | 51.0 |
| Mannitol M200 | 190.3 | 34.3 |
| Sodium Croscarmellose | 27.8 | 5.0 |
| Calcium Stearate | 4.2 | 0.8 |
| Total | 555.6 | 100.0 |

In other formulations, an alternative HPMC product may be used in place of HPMC E3. A diagram for the preparation of hot melt extruded capsules is illustrated in FIG. 1.

5.3. Example 3: Heat Melt Extrusion Formulation 2

Formulation 2 was prepared according to the method of Example 2:

| Formulation 2 | Amount (mg) | % |
|---|---|---|
| Compound A | 50.0 | 7.0 |
| HPMC E3 | 450.0 | 63.0 |
| Mannitol M200 | 173.2 | 24.3 |
| Sodium Croscarmellose | 35.7 | 5.0 |
| Calcium Stearate | 5.4 | 0.8 |
| Total | 714.3 | 100.0 |

In other formulations, an alternative HPMC product may be used in place of HPMC E3.

5.4. Example 4: Heat Melt Extrusion Formulation 3

Formulation 3 was prepared according to the method of Example 2:

| Formulation 3 | Amount (mg) | % |
|---|---|---|
| Compound A | 50.0 | 9.0 |
| PVP VA 64 | 283.3 | 51.0 |
| Mannitol M200 | 190.3 | 34.3 |
| Sodium Croscarmellose | 27.8 | 5.0 |
| Calcium Stearate | 4.2 | 0.8 |
| Total | 556.6 | 100.0 |

5.5. Example 5: Dissolution Profiles of Formulations 1-3

The dissolution profiles of Formulations 1-3 versus control were studied by dissolving the capsule formulations of Compound A in 550 mL of 0.01N HCl and paddle stirring at 75 rpm at 37° C. See FIG. 2. The following capsules were prepared as a control, comprising milled Compound A powder blended with filler, disintegrant and lubricant excipients:

| Control | Amount (mg) | % |
|---|---|---|
| Compound A | 50.0 | 13.2 |
| Silicified Microcrystalline | 79.2 | 20.8 |
| Lactose DC Monohydrate | 237.5 | 62.5 |
| Sodium Croscarmellose | 11.4 | 3.0 |
| Magnesium Stearate | 1.9 | 0.5 |
| Total | 380.0 | 100.0 |

Figure 2:
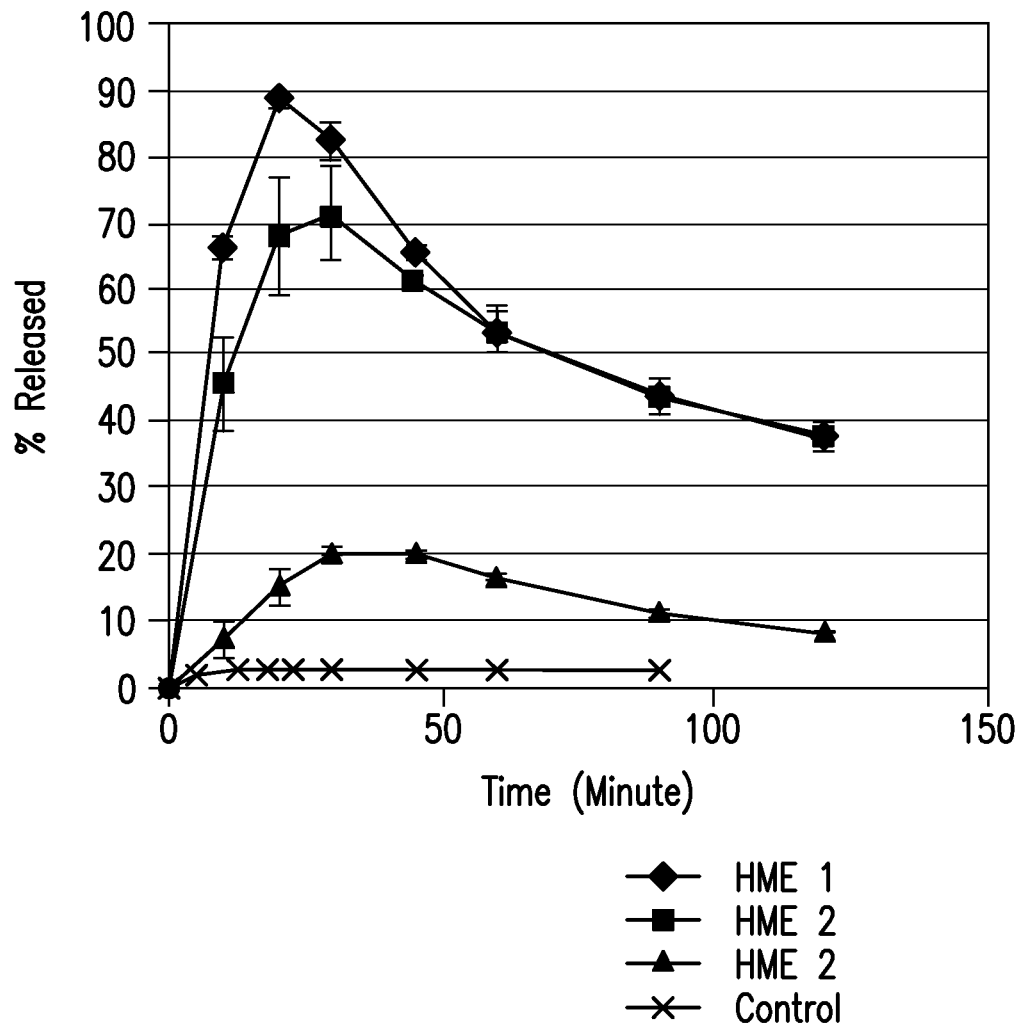
FIG. 2 shows the dissolution profile of Compound A in HME capsule formulations 1 to 3.
Figure 3:
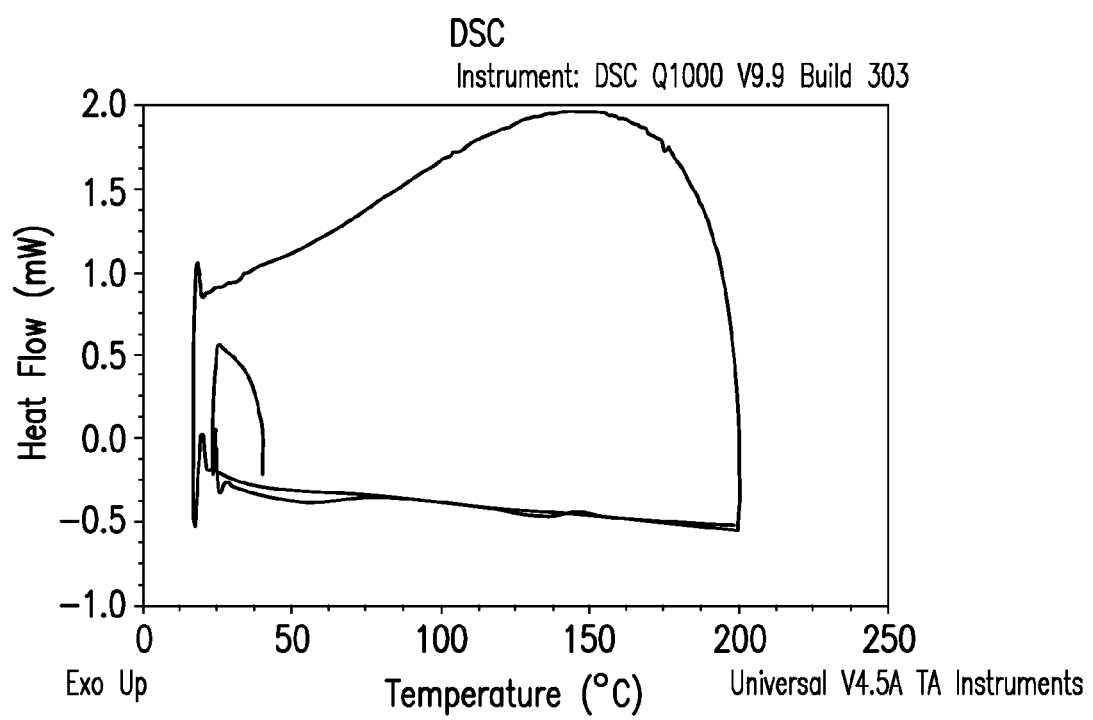
FIG. 3 shows the differential scanning calorimetry plot of spray-dried formulation 5 after storage at ambient temperature for 8 months.
Figure 4:
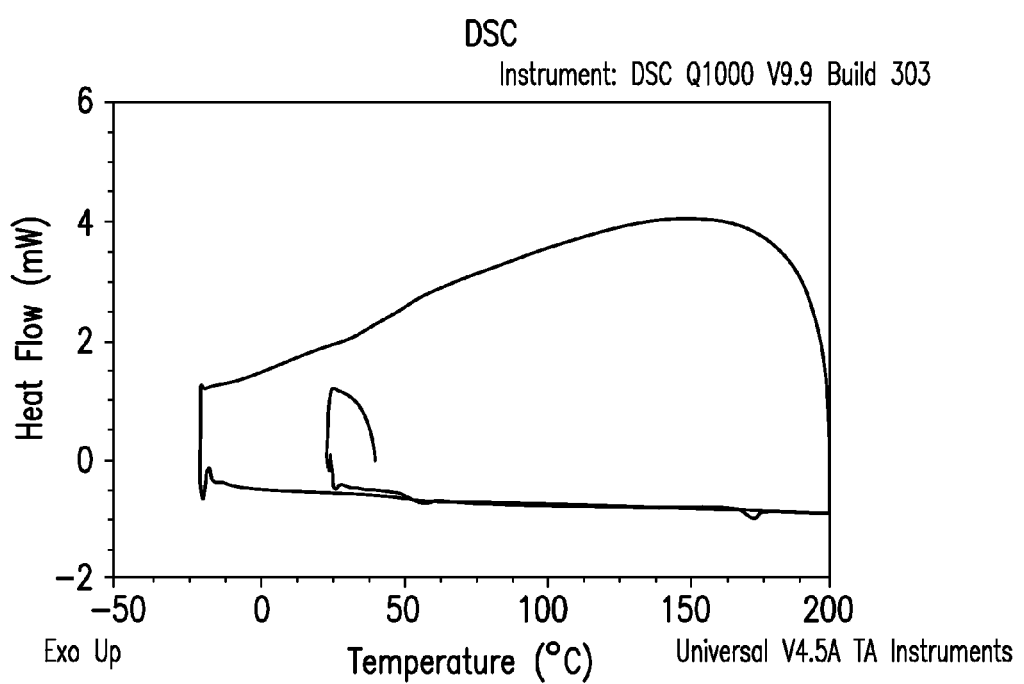
FIG. 4 shows the differential scanning calorimetry plot of spray-dried formulation 6 after storage at ambient temperature for 8 months.
Figure 5:
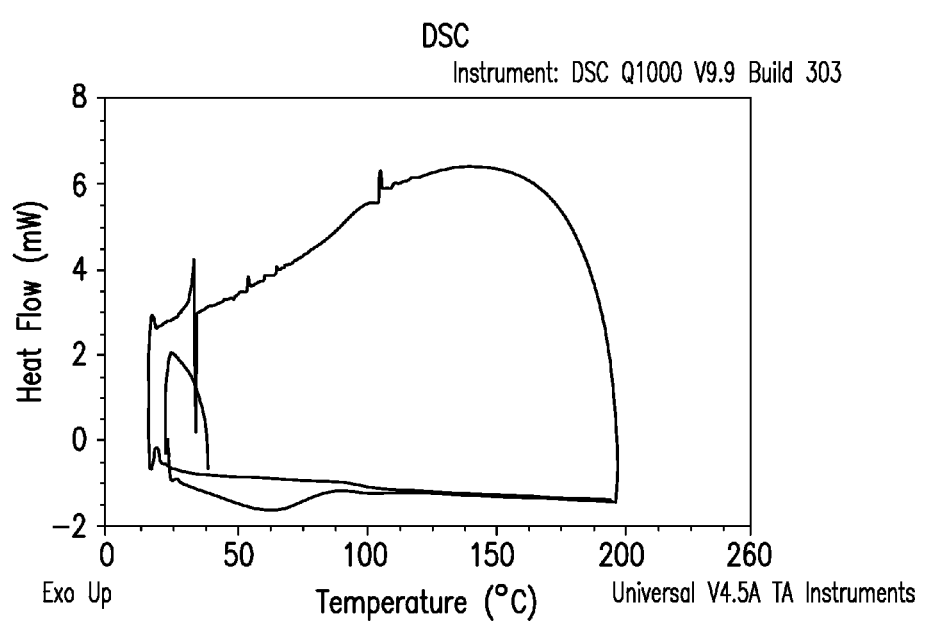
FIG. 5 shows the differential scanning calorimetry plot of spray-dried formulation 7 after storage at ambient temperature for 8 months.
Figure 6:
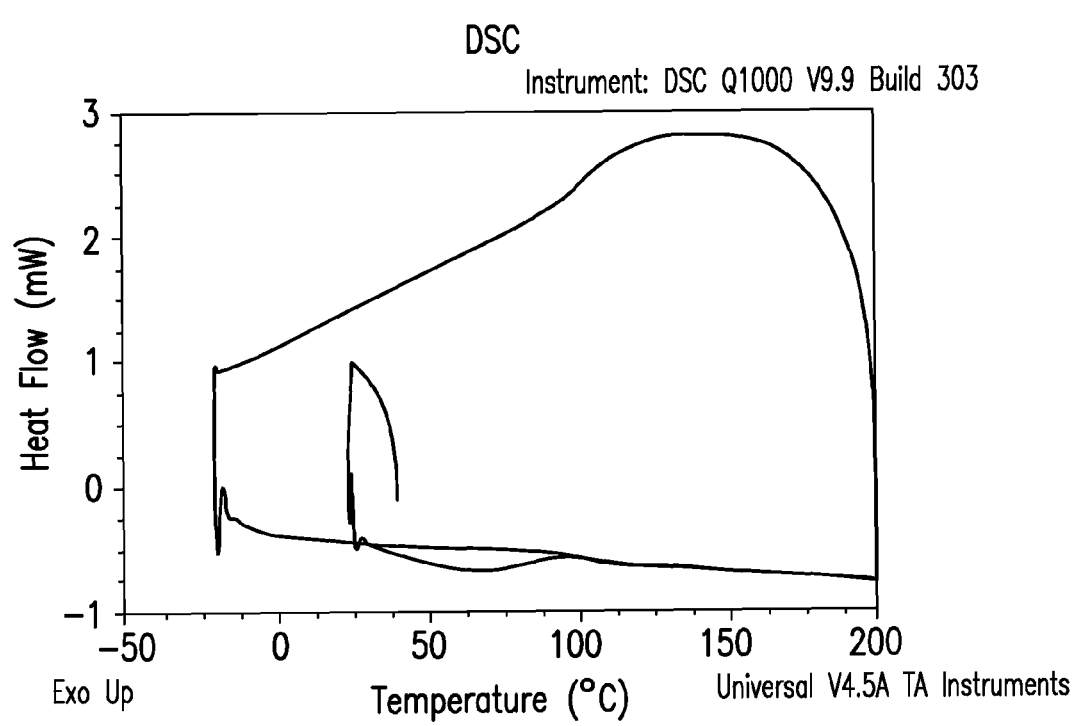
FIG. 6 shows the differential scanning calorimetry plot of spray-dried formulation 8 after storage at ambient temperature for 8 months.
Figure 7:
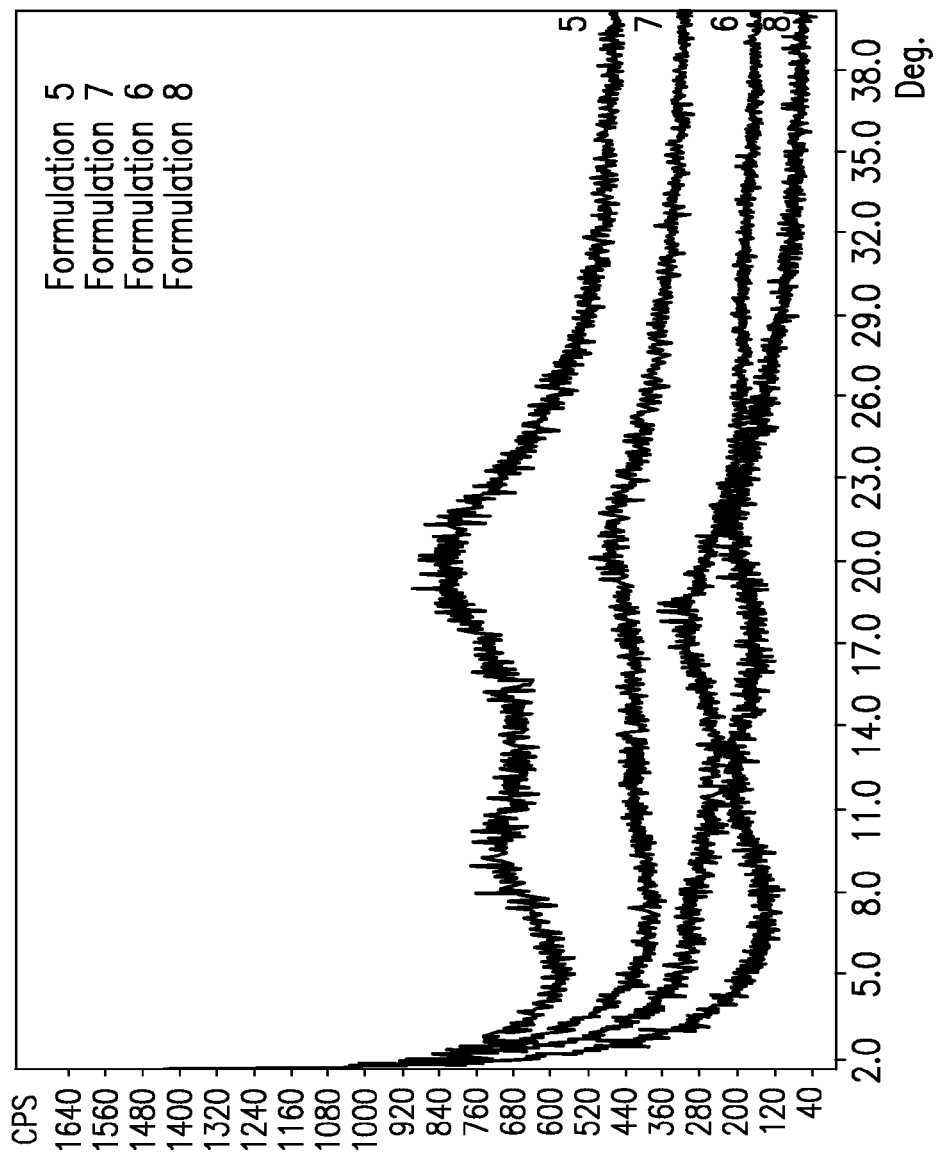
FIG. 7 shows the x-ray powder diffraction pattern of spray-dried formulations 5 to 8 after storage at ambient temperature for 8 months.
Figure 8:
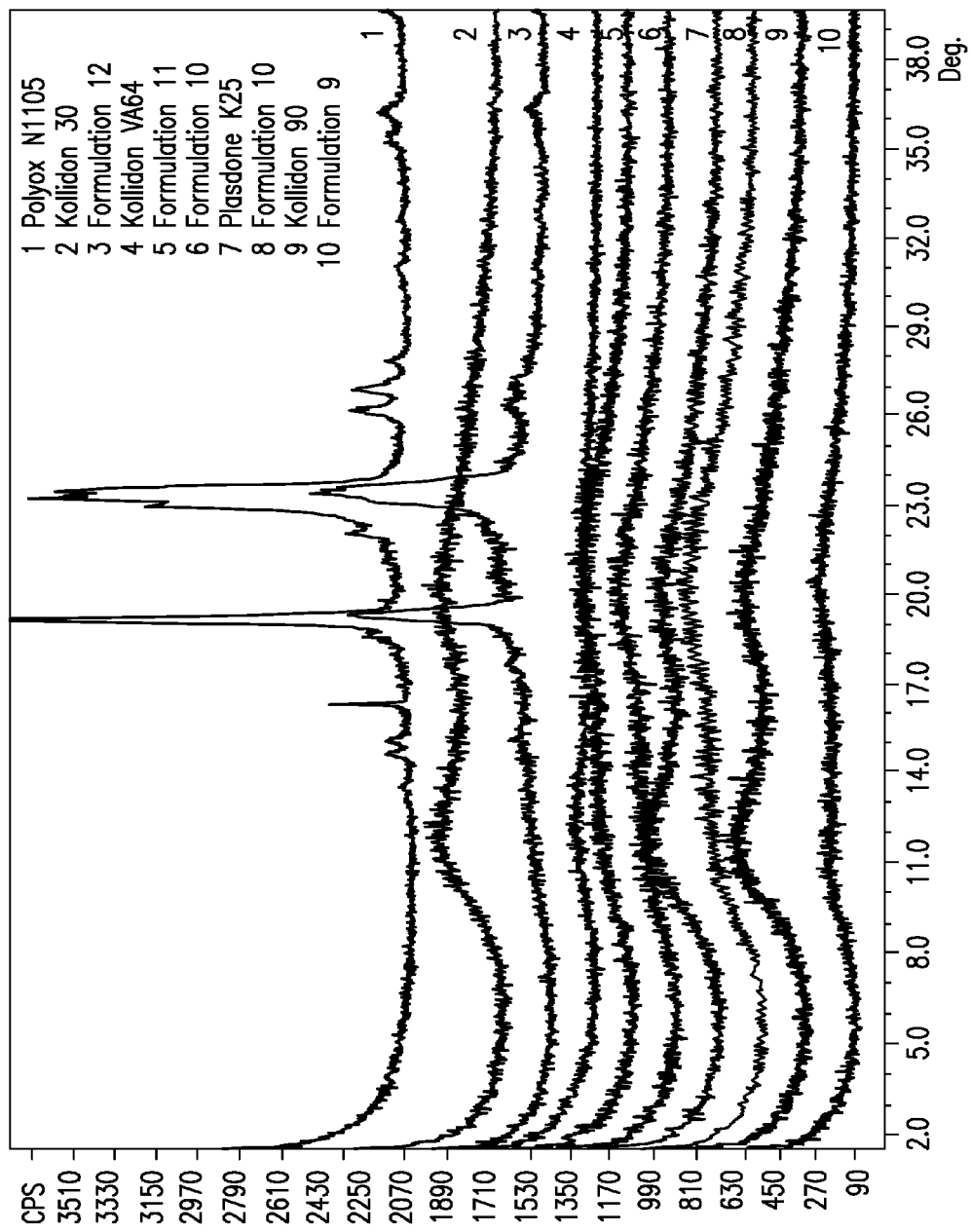
FIG. 8 shows the x-ray powder diffraction pattern of HME formulations 9 to 12.
Figure 9:
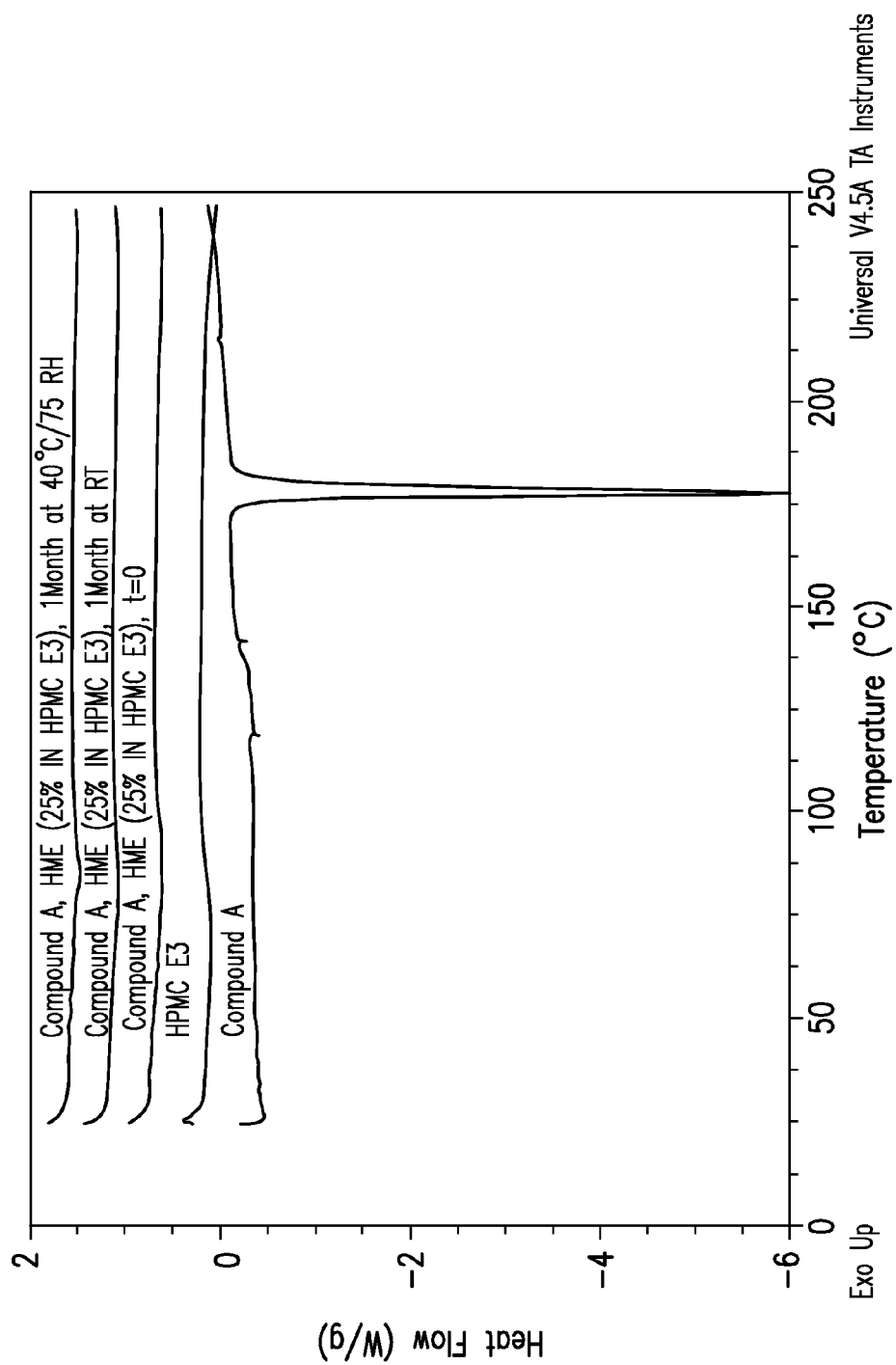
FIG. 9 shows the differential scanning calorimetry plot of HME formulation of Compound A in 25% HPMC E3.
Figure 10:
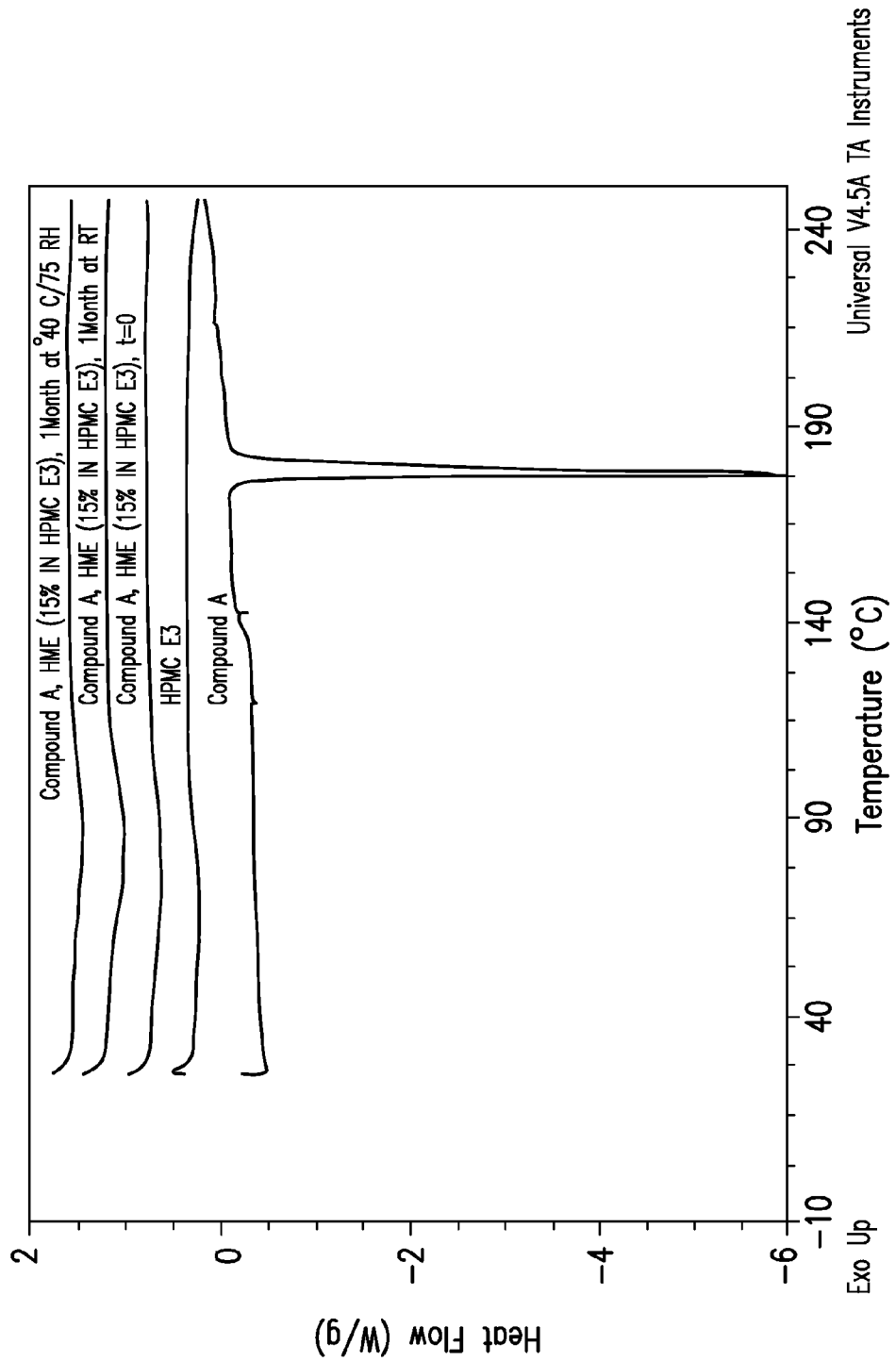
FIG. 10 shows the differential scanning calorimetry plot of HME formulation of Compound A in 15% HPMC E3.

Formulation 1 provided the best dissolution profile, followed by Formulation 2, Formulation 3, and Control. Results are shown in FIG. 2.

5.6. Example 6: Lipid-Based Formulation 4

Formulation 4, a lipid-based formulation of Compound A, was prepared as follows:

1. Melt Vitamin E TPGS and Cremophor RH 40;
2. Combine 56 g of Vitamin E TPGS and 24 g of Cremophor RH 40 and mix well;
3. Combine 3.5 g of Compound A and 63 g of the vehicle prepared in (2);
4. Stir the mixture at 60 C for 30 minutes; and
5. Fill 0.95 g of the product into an 00el gelatin capsule.

| Formulation 4 | Amount (mg) | % |
|---|---|---|
| Compound A | 50.0 | 5.0 |
| Vitamin E TPGS | 661.5 | 66.5 |
| Cremophor RH 40 | 283.5 | 28.5 |
| Total | 995 | 100.0 |

5.7. Example 7: Bioavailabilty Study of Formulations 1-4

Formulations 1-4 were studied for predicted oral bioavailability of Compound A:

| Formulation | Dose (mg/capsule or mg/kg) | Group | Cmax (ng/mL) | Tmax (hr) | $AUC_{0-24}$ (ng * hr/mL) | Relative Exposure (%) |
|---|---|---|---|---|---|---|
| Control | 50 | 1 | 250 (92) | 4 (2-4) | 2154 (1071) | 100 |
| 1 | 50 | 1 | 512 (115) | 4 (4-4) | 6646 (1498) | 308 |
| 2 | 50 | 1 | 513 (88) | 4 (4-6) | 6983 (3084) | 324 |
| Control | 50 | 2 | 199 (43) | 2 (2-4) | 1636 (573) | 100 |
| 3 | 50 | 2 | 446 (116) | 4 (2-4) | 5808 (1917) | 355 |
| 4 | 50 | 2 | 405 (41) | 4 (2-8) | 5537 (1856) | 338 |

Each of Formulations 1-4 enhanced relative exposure of Compound A by over 300%.

5.8. Example 8: Spray-Dry Formulation 5

A spray-dry formulation of Compound A was prepared as follows. A solution of Compound A and HPMC E3 was prepared by stirring 4.0 g of Compound A, 16 g of HPMC E3 and 80 mL of dichloromethane. The resulting solution was spray-dried using a Büchi spray dry system (Büchi Mini Spray Dryer, B-290, Switzerland) according to the following settings: Inlet Temperature 50° C.; Asperator 92%; Pump 30%; Cleaner 0; Airflow 35.

5.9. Example 9: Spray-Dry Formulation 6

A spray-dry formulation of Compound A was prepared as follows. A solution of Compound A and Eudragit® E PO was prepared by stirring 2.0 g of Compound A, 8.9 g of Eudragit® E PO and 100 mL of dichloromethane/ethanol (86:14). The resulting solution was spray-dried using a Büchi spray dry system (Büchi Mini Spray Dryer, B-290, Switzerland) according to the following settings: Inlet Temperature 50° C.; Asperator 92%; Pump 28%; Cleaner 0; Airflow 30.

5.10. Example 10: Spray-Dry Formulation 7

A spray-dry formulation of Compound A was prepared as follows. A solution of Compound A and PVP K12 was prepared by stirring 4.0 g of Compound A, 16.0 g of PVP K12 and 80 mL of dichloromethane. The resulting solution was spray-dried using a Büchi spray dry system (Büchi Mini Spray Dryer, B-290, Switzerland) according to the following settings: Inlet Temperature 50° C.; Asperator 92%; Pump 30%; Cleaner 0; Airflow 35.

5.11. Example 11: Spray-Dry Formulation 8

A spray-dry formulation of Compound A was prepared as follows. A solution of Compound A and Kollidon VA64 was prepared by stirring 1.0 g of Compound A, 10.0 g of Kollidon VA64 and 100 mL of dichloromethane. The resulting solution was spray-dried using a Büchi spray dry system (Büchi Mini Spray Dryer, B-290, Switzerland) according to the following settings: Inlet Temperature 50° C.; Asperator 92%; Pump 30%; Cleaner 0; Airflow 30.

5.12. Example 12: Heat Melt Extrusion Formulation 9

Formulation 9, a solid powder dispersion of Compound A, was prepared as follows: 1. Blend Compound A with Kollidon 90 for 460 rotations using a Turbula® mixer; 2. Process the blended Compound A by heat melt extrusion at 220° C.:

| Formulation 9 | Amount (g) | % |
|---|---|---|
| Compound A | 3.0 | 20 |
| Kollidon 90 | 12.0 | 80 |
| Total | 15.0 | 100.0 |

5.13. Example 13: Heat Melt Extrusion Formulation 10

Formulation 10, a solid powder dispersion of Compound A, was prepared as follows: 1. Blend Compound A with Kollidon 25 for 460 rotations using a Turbula® mixer; 2. Process the blended Compound A by heat melt extrusion at 200° C.:

| Formulation 10 | Amount (g) | % |
|---|---|---|
| Compound A | 3.0 | 20 |
| Kollidon 25 | 12.0 | 80 |
| Total | 15.0 | 100.0 |

5.14. Example 14: Heat Melt Extrusion Formulation 11

Formulation 11, a solid powder dispersion of Compound A, was prepared as follows: 1. Blend Compound A with Kollidon VA 64 for 460 rotations using a Turbula® mixer; 2. Process the blended Compound A by heat melt extrusion at 190° C.:

| Formulation 11 | Amount (g) | % |
|---|---|---|
| Compound A | 3.0 | 20 |
| Kollidon VA 64 | 12.0 | 80 |
| Total | 15.0 | 100.0 |

5.15. Example 15: Heat Melt Extrusion Formulation 12

Formulation 12, a solid powder dispersion of Compound A, was prepared as follows: 1. Blend Compound A with Kollidon 30 and Polyox N1105 for 460 rotations using a Turbula® mixer; 2. Process the blended Compound A by heat melt extrusion at 190° C.:

| Formulation 12 | Amount (g) | % |
|---|---|---|
| Compound A | 3.0 | 20 |
| Kollidon 30 | 6.0 | 40 |
| Polyox N1105 | 6.0 | 40 |
| Total | 15.0 | 100.0 |

5.16. Example 16: Stability of Formulations 1-12

Samples of Formulations 1-12 were stored at ambient temperature. Stability of Compound A over 8 months in each sample was confirmed by X-ray powder diffraction (XRPD) and differential scanning calorimetry (DSC). The results are shown in FIGS. 3-10. Lipid-based formulation (Example 6) was stable at 25° C./60% RH for 1 year. The hot melt extrusion part of Example 2 is stable at 40° C./75% RH and at room temperature for 1 month with proper packaging as indicated by DSC. A formulation similar to that of Example 2, with 25% of Compound A in HPMC, demonstrated similar stability.

5.17. Example 17: Inhibition of PDE4

Phosphodiesterase 4 enzyme was purified from U937 human monocytic cells by gel filtration chromatography, and phosphodiesterase reactions were carried out as previously described. See, e.g., Muller et al., *Bioorg. Med. Chem. Lett.*, 1998, 8(19): 2669-2674. Briefly, reactions were carried out in 96-well deep-well plates in 50 mM Tris HCl pH 7.5, 5 mM $MgCl_2$, 1 µM cyclic adenosine monophosphate (cAMP), plus 10 nM [$^3$H]-cAMP for 45 min at 30° C. The reactions were terminated by boiling, treated with 1 mg/ml snake venom, and separated using AG-1X8 ion exchange resin (BioRad). Reactions consumed less than 15% of available substrate. Compound A inhibited PDE4 with an $IC_{50}$ of 105 nM.

5.18. Example 18: In Vivo LPS-Induced TNF-α Production Assay

Male CD rats procured from Charles River Laboratories at seven weeks of age are allowed to acclimate for one week prior to use. A lateral tail vein is cannulated percutaneously with a 22-gage over-the-needle catheter under brief isoflurane anesthesia. Rats are administered a PDE4 inhibitor of the invention either by intravenous injection via the tail vein catheter or oral gavage 15 to 180 min prior to injection of 0.05 mg/kg LPS (*E. Coli* 055:B5). Catheters are flushed with 2.5 mL/kg of normal injectable saline. Blood is collected via cardiac puncture 90 minutes after LPS challenge. Plasma is prepared using lithium heparin separation tubes and frozen at −80° C. until analyzed. TNF-α levels are determined using a rat specific TNF-α ELISA kit (Busywork). The $ED_{50}$ values are calculated as the dose of the PDE4 inhibitor of the invention at which the TNF-α production is reduced to 50% of the control value. Compound A inhibited TNF-α levels in rat plasma with an approximate $ED_{50}$ of 0.0078 mg/kg p.o.

While the invention has been described with respect to the particular embodiments, it will be apparent to those skilled in the art that various changes and modifications may be made without departing from the spirit and scope of the invention as defined in the claims. Such modifications are also intended to fall within the scope of the appended claims.

Each of the U.S. patents, U.S. patent application publications, foreign patents and foreign published applications recited herein are hereby incorporated by reference in their entirety.

What is claimed is:

1. An oral dosage form consisting of about 9% by weight of a compound of formula (I):

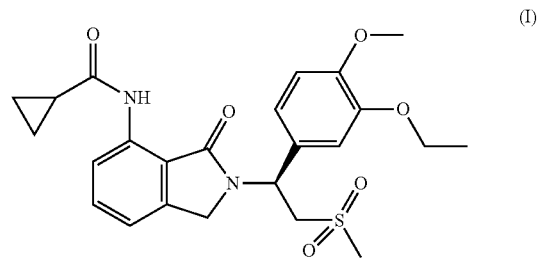 [SMILES: CCOc1cc([C@@H](CS(C)(=O)=O)N2Cc3cccc(NC(=O)C4CC4)c3C2=O)ccc1OC]

or a pharmaceutically acceptable salt thereof, about 34% by weight of mannitol, about 5% by weight of sodium croscarmellose, about 1% by weight of calcium stearate and about 51% by weight of polyvinylpyrrolidone-vinylacetate copolymer.

2. The oral dosage form of claim 1, wherein the oral dosage form is prepared by the following process:
   (i) blend the compound of formula (I) with hydroxypropyl methylcellulose or polyvinylpyrrolidone-vinylacetate copolymer;
   (ii) process the blended product of (i) by hot melt extrusion at 190° C.;
   (iii) mill the extruded product of (ii) using 18 mesh screen;
   (iv) blend the milled extrudate of (iii) with prescreened crosscarmellose sodium and mannitol;
   (v) blend the product of (iv) with prescreened calcium stearate; and
   (vi) encapsulate the blended product of (v).

3. The oral dosage form of claim 2, wherein the blending of steps (i) and (iv) is for 460 rotations each using a shaker mixer.

4. The oral dosage form of claim 2, wherein the blending of step (v) is for 75 rotations using a shaker mixer.

5. The oral dosage form of claim 2, wherein a semi-automatic encapsulator is used in step (vi).

* * * * *